US006505630B1

(12) United States Patent
Sønksen

(10) Patent No.: US 6,505,630 B1
(45) Date of Patent: Jan. 14, 2003

(54) METHOD FOR TREATING URINARY BLADDER DYSFUNCTION

(76) Inventor: Jens Sønksen, Vidnæsdal 14, Holte (DK), DK-2840

( * ) Notice: Subject to any disclaimer, the term of this patent is extended or adjusted under 35 U.S.C. 154(b) by 30 days.

(21) Appl. No.: 09/591,962

(22) Filed: Jun. 12, 2000

Related U.S. Application Data

(60) Provisional application No. 60/195,023, filed on Apr. 6, 2000, provisional application No. 60/187,847, filed on Mar. 8, 2000, and provisional application No. 60/139,010, filed on Jun. 14, 1999.

(51) Int. Cl.[7] .................................................. A61B 19/00
(52) U.S. Cl. .......................................... 128/898; 601/46
(58) Field of Search ......................... 128/DIG. 25, 898; 601/45, 46; 600/29-32, 38-41, 552

(56) References Cited

U.S. PATENT DOCUMENTS

| | | | | |
|---|---|---|---|---|
| 4,911,149 A | | 3/1990 | Borodulin et al. | |
| 5,782,745 A | | 7/1998 | Benderev | |
| 5,853,362 A | * | 12/1998 | Jacobs | 600/38 |
| 6,030,338 A | * | 2/2000 | Benderev | 600/30 |
| 6,159,170 A | * | 12/2000 | Borodulin et al. | 601/101 |
| 6,258,373 B1 | * | 7/2001 | Cutler | 424/434 |

OTHER PUBLICATIONS

Dasgupta, P., Haslam, C., Goodwin, R., Fowler, C.F.; "The 'Queen Square bladder stimulator': a device for assisting emptying of the neurogenic bladder"; British Journal of Urology; (1997) vol. 80, issue 2, pp. 234–237.*

Sonksen et al., Ejaculation by vibratory stimulation in SCImen, 1994, pp. 651–660.

* cited by examiner

*Primary Examiner*—David J. Isabella
*Assistant Examiner*—Urmi Chattopadhyay
(74) *Attorney, Agent, or Firm*—Merchant & Gould P.C.

(57) ABSTRACT

A method for treating urinary bladder dysfunction by mechanical vibration of the external genital area.

6 Claims, 1 Drawing Sheet

METHOD FOR TREATING URINARY BLADDER DYSFUNCTION

This application claims benefits to U.S. application Ser. No. 60/195,023, filed Apr. 6, 2000, which claims benefits to U.S. application Ser. No. 60/187,847, filed Mar. 8, 2000, which claims benefits to U.S. application Ser. No. 60/139,010, filed Jun. 14, 1999.

TECHNICAL FIELD

This invention relates to treatment of urinary bladder dysfunction including urinary incontinence.

BACKGROUND OF THE INVENTION

U.S. Pat. No. 4,911,149 gives a background of the invention as stated in the following.

The Therapeutic Effects of Vibratory Stimulation

The therapeutic effects of vibratory stimulation on the human body have been documented. Vibration applied to tissue increases blood circulation due to the increase in capillary dilation. The increased blood flow increases the consumption of oxygen and nutrients by muscles and improves the regeneration process. The result is an improved muscular tone, elasticity and contractile capacity. In addition, vibratory stimulation reduces tissue swelling, enhances healing of wounds and results in effective anti-inflammatory action.

The physiological effect of low frequency vibratory stimulation varies depending on frequency, amplitude and duration of its application. Depending on the structure of the muscles (smooth or striated), the same dose of local vibratory stimulation may cause either contraction or relaxation. A low frequency mechanical vibration of between 60 and 200 Hz applied to skeletal muscle induces a sustained contraction of the muscle and a simultaneous relaxation of its prime antagonists. This tonic vibratory reflex (TVR) is elicited in normal spastic, paretic and myotonic muscles alike. Within the 60 and 200 Hz range, the vibration reduces the contractile force and tension of smooth muscle.

The most common therapeutic uses of vibratory stimulation involve external application of the vibratory forces. Vibratory stimulation is used for treating neuromuscular motor dysfunction in patients with cerebral palsy. External vibration is also used for treating patients with cervical osteochondrosis, lumbosacral radiculitiis, postamputation contracture, sequelae of lesions of the long tubular bones, and chronic dental pain. Externally applied abdominal vibration is used for improving efficiency in peritoneal dialysis and for simulating intestinal mobility in cases of intestinal atonia. External vibratory stimulation is also useful for bladder voiding in paralysed patients.

Vibratory stimulation has also been used internally to relax and dilate the cervix prior to abortion or birth. Vibration accelerates expansion of the cervical opening, thereby facilitating parturition. The vibration is applied directly to the cervical muscle, and the source of the vibration is withdrawn as soon as the cervical dilation is achieved.

Vibration sources vary with the application. External vibration may be applied by large flat or rounded vibrating machines designed to be placed against the appropriate body parts. Internal vibratory stimulation of the cervix, on the other hand, may be applied by a vibrating spatula or a vibrating bullet shaped applicator placed against the wall of the cervical muscle.

Internally applied vibratory stimulation has been proposed for treating internal muscle and connective tissue disorders such as urethral strictures, urinary and anal incontinence, unstable bladder and urethral syndrome, see U.S. Pat. No. 4,311,149 to Borodulin et al. and U.S. Pat. No. 5,782,745 to Benderev.

Externally applied penile vibratory stimulation has been used to induce ejaculation in men with spinal cord injuries, see J. Sønksen, F. Biering-Sørensen and J. K. Kristensen "Ejaculation induced by penile vibratory stimulation in men with spinal cord injuries. The importance of the vibratory amplitude", Paraplegia 32 (1994) 651–660.

Urinary Incontinence

Urinary incontinence is a symptom of urinary bladder dysfunction which relates to urethral sphincter dysfunction and/or abnormalities of detrusor contractions. Other conditions including for example urinary bladder hyperreflexia, urinary bladder high storage pressure, low urinary bladder capacity and urinary high flow pressure are also a part of the urinary bladder dysfunctional scenario.

Urinary incontinence is a distressing and previously neglected condition that can result from a range of pathological processes in the central or peripheral nervous system, the bladder, or the urethra. The disorder is related to faulty storage or deficient control and is difficult to treat.

Incontinence can affect all ages. Several reports have according to U.S. Pat. No. 4,911,149 shown that 16–50% of nonporous females admit to the loss of a small amount of urine during hard coughing, laughing, or sneezing, particularly if the bladder is excessively full. Five percent of women between the ages of 15–34 and about 10 to 26% in ages of 35–60 reported regular troublesome stress urinary incontinence. As is shown by both European and American researchers, urinary incontinence is a problem affecting 10 to 40% of the elderly women in the community and up to 50% of the elderly in institutions. Urinary incontinence is therefore a major geriatric problem with substantial medical and social implications.

Stress urinary incontinence is defined as the involuntary loss of urine through the intact urethra as the result of a sudden increase in intra-abdominal pressure in the absence of bladder activity. Stress urinary incontinence accounts for roughly 75% of all female urinary incontinence.

The most frequent cause of stress urinary incontinence in females is dysfunction of the sphincteric mechanism of the urethra and an inadequate pelvic floor function. The key factor in the development of stress incontinence in females is an inherent weakness in the mechanism of urinary continence upon which precipitating factors exert influence. Typically the problem occurs in women in whom childbirth causes long-term anatomic damage and a relaxation in the pelvic and periurethral musculature.

The percentage of such women comprises 52.2% of the total number of stress urinary incontinence sufferers.

Menopause is another very important precipitating factor in the development of stress incontinence. Hormonal dysfunction in postmenopausal women is characterized by estrogen deficiency and leads to atrophy of pelvic tissues. This can distort local anatomy and result in stress incontinence.

Abnormal and involuntary detrusor contractions are also a common cause of urinary frequency, urgency, nocturia, bed-wetting, urge incontinence, and the like. Abnormalities of detrusor contraction may be of neurogenic or non-neurogenic (e.g. myogenic, psychologic or idiopathic) origin. In the absence of a neurologic lesion, the condition is termed "detrusor instability". The unstable bladder is a very common problem affecting as much as 10% of the population and a substantially higher percentage at the two extremes of life. In most cases the aetiology of the detrusor instability remains unknown, since these patients are referred to as having "idiopathic" detrusor instability. As a result, the treatment of detrusor instability is difficult.

Conventional treatment of urinary incontinence falls into five main categories: surgery, drug therapy, electrical stimulation, re-education, and—where necessary—the use of protective clothing, tampons, vaginal appliances designed to support the urethra, and indwelling catheters. These treatments are discussed below. There are over 50 surgical procedures designed to correct urinary incontinence. The success of these procedures, however, is much higher in younger women than in the elderly. Approximately 10–40% of women who undergo surgical correction of urinary stress incontinence will have recurrent urinary incontinence and other voiding difficulties. Surgery is not effective when the problem is an unstable bladder or intrinsic urethral abnormalities, and the condition of the patient after surgery in this case can worsen.

The surgical method is generally accepted as the most appropriate treatment for severe female genuine stress incontinence. In a number of cases, this method is also used for treating patients with a mild-to-moderate form of incontinence.

The trend in the profession, however, is to avoid surgical therapy if possible. In addition, there are some patients for whom surgery is inappropriate. For example, women who wish further pregnancies would be poor candidates since later vaginal deliveries may adversely affect successful surgery.

New surgical techniques such as electronic stimulation of sphincters and implantations of artificial sphincters are widely used for treating patients with urinary incontinence caused by surgical traumas or by organic neurologic dysfunctions. Although these new methods give promising results, they still require further clinical studies as well as improvements in devices necessary for implementation of these methods.

Drugs of several types also have been recommended for treating stress urinary incontinence. These drugs are nonspecific, however, and therefore act on structures and viscera other than the bladder and urethra. Large doses are often required, and toxicity can easily be reached before the desired effect on the bladder and urethra is achieved. Moreover, even when drug treatment is effective, it does not lead to restoration of a normal micturition pattern.

Re-education for incontinence includes bladder retaining programs and re-education of the pelvic floor muscles. The bladder re-training method consists of instituting a program of scheduled voidings with a progressive increase in the interval between each micturition. A four to six week treatment program is common.

Two different methods of electrical stimulation for the correction of urinary incontinence are still according to U.S. Pat. No. 4,911,149 in use and are classified according to the time of application and the intensity of electrical stimuli; long-term, or chronic, electrical stimulation and short-term or maximum electrical stimulation. Long-term electrical stimulation is continued 6–20 hours daily for prolonged periods of from 3 to 36 months and short-term or maximum electrical stimulation is continued 20–30 minutes over a one-month period, the stimulation being applied 1–5 times a day. Electro-stimulation has been found to be valuable in cases of urinary urge incontinence due to detrusor instability since it is more effective than drug treatment and can produce re-education of incontinence. The mechanisms behind this curative effect are not yet defined, however.

Exercise therapy, which is a natural biological and non-invasive functional method of treatment, plays a leading role in non-surgical methods of treatment of stress urinary incontinence, as this method positively affects a weakened muscular-ligamentous apparatus of the pelvic floor. The exercise is designed to strengthen the urethral and periurethral striated muscles. Physiotherapy consists of four or five pelvic floor contractions repeated every hour and interrupted micturition practiced on each occasion. In the beginning, the treatment is carried out on a hospital basis for four weeks followed by self-treatment for a prolonged period of time.

Internal vibratory stimulation as proposed by Borodulin and Benderev always involves a certain risk for infection of the body cavities. Further it is difficult to use these methods for self-treatment.

As a rule, all the non-surgical methods of treatment of urinary incontinence described above are lengthy and require repeated courses of treatment. In addition, the long-term results of these types of treatment are largely unsuccessful. In spite of a large number of investigations dedicated to urinary incontinence, this problem is still far from being resolved.

SUMMARY OF THE INVENTION

The present invention solves significant problems in the art by providing a method for treating urinary bladder dysfunction by effective mechanical vibration or stimulation of the external genital area. By external genital area we mean clitoris and/or surroundings for women and fraenulum praeputii and/or surroundings for men. Perhaps even stimulation of perineum has an effect.

The method is useful for treating urinary bladder dysfunction caused by abnormal urinary detrusor contractions and urethral sphincter dysfunction originating from neurogenic, (e.g. spinal cord injury, scleroses and other neurogenic dysfunctions) as well as non-neurogenic (e.g. stress or urge) causes.

Repeated treatment with vibratory stimulation in spinal cord injured persons is expected to preserve kidney function due to a reduced urinary bladder storage pressure.

Furthermore, it is expected that vibratory stimulation will have similar or identical effects on urinary bladder dysfunction whether or not ejaculation/pseudoorgasm (see EXPERIMENTAL III in the following) is induced.

DETAILED DESCRIPTION OF THE INVENTION

Figure 1:
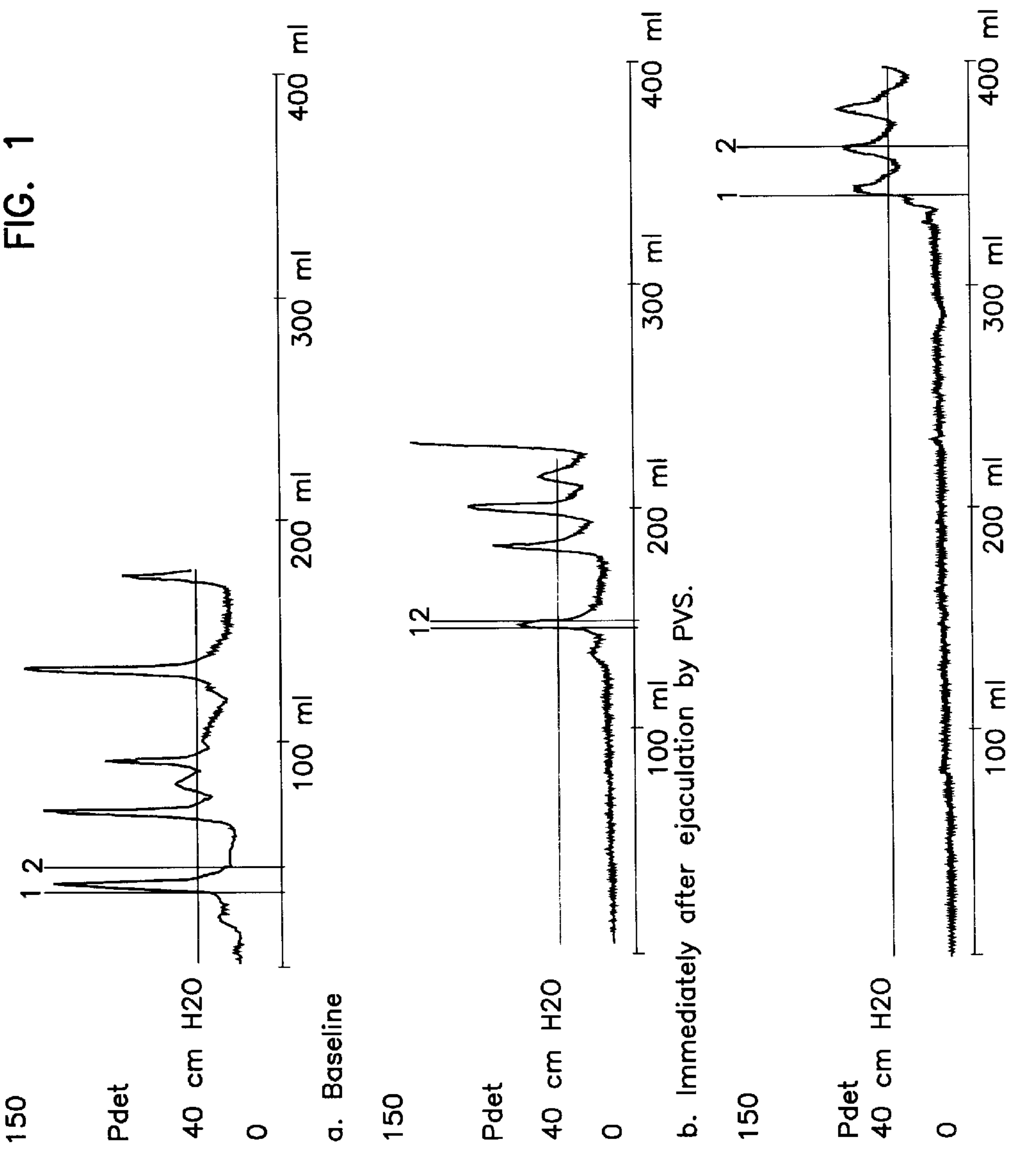
FIG. 1 shows the relation between detrusor pressure (Pdet) and the volume instilled in the bladder (velocity 50 ml/min) at a: Baseline, b: Immediately after ejaculation by PVS and c: After 1 month of repeated ejaculation by PVS every third day.

External vibratory stimulation is performed daily (or with days interval) for periods of 0.1 to 5 minutes, typically 3 minutes, and the maximum numbers of stimulation periods are usually 6 per day. This corresponds with a daily total stimulation of up to 30 minutes. The vibratory stimulation parameters include at least one frequency ranging between about 60 Hz and about 200 Hz, including frequency bands, preferably about 100 Hz. This also includes randomised frequency bands. The vibratory peak-to-peak amplitude is normally ranging between 0.5 and 3.5 mm. However, there may be individual variation in the stimulation time, frequency and amplitude also outside these values. Thus, it is expected that there may be effect on urinary bladder dysfunction by mechanical vibratory stimulation outside this frequency interval and amplitude interval.

The mechanical vibration or stimulation can for example be performed by a vibrator source as known from international patent application no. WO 96/32916.

A physician, physiotherapist, nurse or the like can operate the vibrator source, but normally the patient himself/herself can operate the vibrator after instruction.

EXAMPLES

Experimental

Experiments have been performed on human beings with spinal cord injuries, but similar results are expected on human beings without spinal cord injuries.

The following experiments were performed by vibration with a vibrator type "Ferticare Personal Care" from the firm Multicept, Hoersholm, Denmark. The frequence was 100 Hz and the vibratory peak-to-peak amplitude 2.5 mm. The treatment was performed to ejaculation/pseudoorgasm using an average time of one minute. Furthermore in EXPIRIMENTAL II the same stimulation was performed twice a week or every third day during four weeks.

Experimental I

Inhibition of the Urinary Bladder Detrusor Contractions During and Following Penile Vibratory Stimulation and Ejaculation in Spinal Cord Injured Males The physiological events of ejaculation induction procedures in spinal cord injured men were studied and the dynamic activity of the internal and external urinary sphincters' pressures was measured during penile vibratory stimulation.

Nine spinal cord injured men were recruited for the study. Simultaneous recording of the internal and external urinary sphincters' pressures with standard urodynamic catheters during fluoroscopic control was performed. The vibratory stimulation parameters were: frequency: 100 Hz and peak-to-peak amplitude: 2.5 mm.

The following observations were noted: Detrusor activity and involuntary emptying of the urinary bladder during instillation (via urethral catheter) of the 50 ml to 105 ml of contrast fluid into the urinary bladder were observed in four men with a history of urinary bladder instability. Subsequently, penile vibratory stimulation was initiated during the next trial of contrast fluid instillation and it was then possible to instill contrast fluid up to a volume level of 275 ml to 400 ml without any detrusor activity. Ejaculation was induced in three men whereas one man failed to obtain ejaculation. No detrusor activity was seen in the urinary bladder after ejaculation and discontinuation of penile vibratory stimulation. A similar response was seen in the man who did not obtain ejaculation.

The results of the invention are shown in FIG. 1 of the drawing. The graphs show the relation between the detrusor pressure (Pdet) and the volume installed in the bladder (velocity 50 ml/min.) in a man with a spinal cord injury, a) untreated, b) immediately after ejaculation by penile vibratory stimulation (PVS) and c) after 1 months of repeated vibratory stimulation every third day. 1 shows the bladder volume tolerance defined as the maximum volume installed with detrusor pressures remaining below 40 cm $H_2O$. 2 shows the bladder capacity before involuntary leaking. It is evident that the bladder capacity has increased by PVS.

Experimental II

Effects of Vibratory Stimulation on Urinary Bladder Detrusor Contractions in Spinal Cord Injured Aim: To examine the effects of penile vibratory stimulation (PVS) until ejaculation on urinary bladder hyperreflexia in spinal cord injured men.

Methods: Four men with spinal cord lesion ranging from C4 to T7 have been included. Cystometry was performed before (baseline) and after ejaculation by PVS and was repeated following one month of frequent ejaculation by PVS (twice per week). A peak-to-peak amplitude of 2.5 mm and a frequency of 100 Hz was used for PVS.

Results: An average of 1 minute of PVS was used to induce ejaculation. Baseline cystometry demonstrated bladder hyperreflexia and external sphincter dyssynergia in all subjects. In one person there was no effect on bladder hyperreflexia following ejaculation by PVS. In 3 men the volume tolerance of the bladder, defined as the maximum volume instilled with bladder pressures remaining below 40 cm $H_2O$, increased from an average (range) of 117 ml (60–170) at baseline to 346 ml (160–700) immediately after ejaculation by PVS and 406 ml (180–700) after one month of frequent stimulation, respectively. Since PVS had not been performed in the 48 hours preceding the final cystometric study, the effect of PVS appears to persist to at least that time interval. The typical pattern of the relation between detrusor pressure and the volume instilled in the bladder is shown in FIG. 1 printed for one of the men.

Experimental III

The same experiment as in experimental II has been performed in two spinal cord injured females with vibratory stimulation of the clitoris. An average of 1 minute of vibratory stimulation was used to induce an autonomic reflex response (termed "pseudoorgasm" in the following text) characterized by rhytmic abdominal muscle and leg contractions, which is similar to the response seen in males. Following vibratory stimulation and pseudoorgasm the same effects on the urinary bladder as in experimental I and II were seen in both females.

CONCLUSION OF THE EXPERIMENTS

Conclusions

During and following vibratory stimulation (with or without ejaculation/pseudoorgasm) the urinary bladder capacity has been significantly increased and the urinary bladder storage pressure significantly reduced through inhibition of the urinary bladder detrusor contractions in spinal cord injured persons with detrusor hyperreflexia. This will have implications in the management of incontinence cases and in persons at risk for upper urinary tract deterioration originating from high urinary bladder storage pressure.

Consequently, repeated treatment with vibratory stimulation in spinal cord injured persons is expected to establish urinary continence due to inhibition of abnormal detrusor contractions and higher urinary bladder capacity and to preserve kidney function due to a lower urinary bladder storage pressure.

Furthermore, it is expected that mechanical vibratory stimulation with or without ejaculation/pseudoorgasm will have similar or identical effects on urinary bladder dysfunction in persons with other neurogenic causes than spinal cord injury as well as in persons with non-neorogenic causes of urinary bladder dysfunction.

It is also expected that mechanical vibratory stimulation of the external genital area will have a beneficial effect on anal incontinence.

What is claimed is:

1. A method for treating urinary bladder dysfunction, wherein human beings with such dysfunction are treated by effective mechanical vibratory stimulation of the external genital area wherein the vibratory stimulation is delivered with a vibratory peak-to-peak amplitude ranging between about 0.5 mm and about 3.5 mm.

2. A method according to claim 1 for treating urinary bladder dysfunction, wherein urinary bladder dysfunction results from the group consisting of: abnormalities of urinary detrusor contractions of neurogenic or non-neurogenic origin, urethral sphincter dysfunction of neurogenic or non-neurogenic origin, bladder hyperreflexia, urinary bladder high storage pressure, low bladder capacity, urinary bladder high flow pressure, incontinence, stress incontinence, urge incontinence, urinary frequency, urgency and nocturia.

3. A method for treating urinary bladder dysfunction according to claim 1, wherein human beings are treated by effective mechanical vibration of clitoris and/or surroundings or fraenulum praeputii and/or surroundings.

4. A method for treating urinary bladder dysfunction according to claim 3, wherein human beings are treated by effective mechanical vibration for 0.1 to 5.0 minutes, up to 6 times a day.

5. A method for treating urinary bladder dysfunction according to claim 3, wherein the vibratory stimulation is performed with at least one frequency ranging between about 60 and about 100 Hz.

6. A method for treating anal incontinence, where human beings are treated by effective mechanical vibration of the external genital area, wherein the vibration is delivered with a vibratory peak-to-peak amplitude ranging between about 0.5 mm and about 3.5 mm.

* * * * *